(12) United States Patent
Torrie et al.

(10) Patent No.: US 7,832,401 B2
(45) Date of Patent: Nov. 16, 2010

(54) HIP DISTRACTION

(75) Inventors: Paul Alexander Torrie, Marblehead, MA (US); Edward J. Daley, II, Maynard, MA (US); Paul J. Skavicus, Maynard, MA (US)

(73) Assignee: Smith & Nephew, Inc., Memphis, TN (US)

( * ) Notice: Subject to any disclaimer, the term of this patent is extended or adjusted under 35 U.S.C. 154(b) by 1256 days.

(21) Appl. No.: 11/289,705

(22) Filed: Nov. 30, 2005

(65) Prior Publication Data

US 2007/0161935 A1  Jul. 12, 2007

(51) Int. Cl.
- A61G 15/00 (2006.01)
- A61F 5/37 (2006.01)
- A47B 71/00 (2006.01)
- A47B 7/00 (2006.01)
- A47C 17/86 (2006.01)

(52) U.S. Cl. .................. 128/845; 128/846; 128/882; 5/600; 5/648; 5/621; 5/624

(58) Field of Classification Search .............. 128/845, 128/846, 882; 5/600, 648, 621, 624; 606/57, 606/54, 55, 105; 602/32, 35
See application file for complete search history.

(56) References Cited

U.S. PATENT DOCUMENTS

| | | | |
|---|---|---|---|
| 2,691,979 A | 10/1954 | Watson | |
| 3,020,909 A | 2/1962 | Stevens | |
| 3,606,884 A * | 9/1971 | Peter | 602/24 |
| 4,407,277 A * | 10/1983 | Ellison | 602/39 |
| 4,681,309 A | 7/1987 | Lechner | |
| 4,872,656 A * | 10/1989 | Brendgord et al. | 5/601 |
| 4,913,413 A | 4/1990 | Raab | |
| 4,940,218 A | 7/1990 | Akcelrod | |
| 4,964,400 A | 10/1990 | Laico et al. | |
| 5,025,802 A | 6/1991 | Laico et al. | |
| 5,027,799 A | 7/1991 | Laico et al. | |
| 5,500,964 A * | 3/1996 | Bergersen | 5/607 |
| 5,515,562 A | 5/1996 | Miller et al. | |

(Continued)

FOREIGN PATENT DOCUMENTS

CH    449174 A * 12/1967

(Continued)

OTHER PUBLICATIONS

International Preliminary Report on Patentability for PCT/IB2006/004038, dated Jun. 12, 2008 (7 pages).

(Continued)

*Primary Examiner*—Patricia M Bianco
*Assistant Examiner*—O. Hawthorne
(74) *Attorney, Agent, or Firm*—Fish & Richardson P.C.

(57) ABSTRACT

An apparatus includes a distractor assembly adapted to couple to a leg and capable of providing a distraction load on the leg in both supine and lateral positions of the leg. The assembly is coupled to a surgical table by a ball joint or a universal joint. A method includes coupling a leg to a distractor assembly, positioning the leg in one of a distraction mode and a femoral acetabular impingement mode, and repositioning the leg in the other of the modes without the need for accessing a draped pelvis/thigh region.

38 Claims, 16 Drawing Sheets

U.S. PATENT DOCUMENTS

| | | | |
|---|---|---|---|
| 5,608,934 A * | 3/1997 | Torrie et al. | 5/624 |
| 5,645,079 A | 7/1997 | Zahiri et al. | |
| 5,926,878 A | 7/1999 | Morton et al. | |
| 6,058,534 A * | 5/2000 | Navarro et al. | 5/648 |
| 6,378,149 B1 | 4/2002 | Sanders et al. | |
| 6,654,974 B2 | 12/2003 | Ruehl et al. | |
| 6,671,905 B2 | 1/2004 | Bartlett et al. | |
| 6,895,969 B2 | 5/2005 | Malcolm et al. | |
| 2002/0133979 A1 * | 9/2002 | Gantier | 36/72 R |
| 2004/0123389 A1 * | 7/2004 | Boucher et al. | 5/623 |
| 2004/0133979 A1 * | 7/2004 | Newkirk et al. | 5/600 |
| 2004/0133983 A1 | 7/2004 | Newkirk et al. | |
| 2005/0160533 A1 | 7/2005 | Boucher et al. | |
| 2006/0185090 A1 * | 8/2006 | Jackson | 5/621 |
| 2007/0251011 A1 * | 11/2007 | Matta et al. | 5/624 |

FOREIGN PATENT DOCUMENTS

| | | |
|---|---|---|
| CH | 449 174 | 4/1968 |
| WO | 2007/021806 | 2/2007 |

OTHER PUBLICATIONS

Arthrex Product Info, Knee & Hip, Hip Distractor and Disposables Kit, 1 page.
"Hip Distractor: Assembly and Set-Up Instructions", Innomed, 2003, 2 pages.
"Stulberg Hip Positioner", Innomed, Inc., 1 page.
"Wixson Hip Positioner", Innomed, Inc., 1 page.
"Cherf Leg Holder", Innomed, 2000, 1 page.
"Multi-Adjustment Hip Positioner", Innomed, 2002, 1 page.
"Adjustable Leg Support Stand", Innomed, 2002, 1 page.
"Assistant Free Robb Leg Positinoer", Innomed, 2005, 1 page.
"Assistant Free Stulberg Leg Positioner", Innomed, 2000, 2 pages.
"Cambridge Hip Distracter", Sovereign Insttruments, Ltd., 2 pages.
International Search Report, PCT/WO2007/080454 dated Jul. 19, 2007, 4 pages.

* cited by examiner

HIP DISTRACTION

TECHNICAL FIELD

This invention relates to hip distraction.

BACKGROUND

To gain access to the hip joint to perform hip arthroscopy, the femoral head (ball) is pulled out of the acetabulum (socket) in the pelvis. Hospitals typically use a fracture table to put the hip joint under traction while the patient is in a supine position. Hip distractors are known that attach to a standard operating table, and that are dedicated to use with the patient in either a supine position or a lateral position.

Two methods for hip distraction are Distraction Mode, in which the lower extremity is put in tension via traction between the foot and pelvis, and Femoral Acetabular Impingement (FAI) Mode, in which there is no traction on the lower extremity and there is a larger range of motion than the distraction mode. In the FAI Mode, the hip is flexed up between 30 to 90 degrees and the knee is flexed approximately 45 degrees. The scrub nurse holds the knee from falling laterally. Both methods can be performed using a fracture table with the patient in the supine position. To move a patient between the two modes, and to move the hip joint through its range of motion to check for impingement between the femoral neck and the acetabular rim, the circulator nurse reaches under the draped foot area to unlock the table.

SUMMARY

According to one aspect, an apparatus includes a distractor assembly adapted to couple to a leg and capable of providing a distraction load on the leg in both supine and lateral positions of the leg.

Embodiments of this aspect may include one or more of the following features. The distractor assembly includes a joint, for example, a ball joint or universal joint, configured to couple the distractor assembly to a surgical table. The joint is lockable and the mechanism for locking the joint is located remote from the joint. The apparatus is configured such that with a patient positioned on the surgical table and coupled to the distractor, the joint is offset from the patient's hip joint. The apparatus is entirely supported by a surgical table.

In an illustrated embodiment, the distractor assembly includes a distractor member and a leg mount, for example, a foot mount, coupled to the distractor member for movement relative to the distractor member by both sliding and threaded engagement. The leg mount is coupled to the distractor member by a ball joint. The apparatus includes a foot holder mountable to the distractor assembly and including a support bar that supports the lower leg in the lateral and supine positions.

The apparatus further includes a support configured to be fastened to a surgical table, and the distractor assembly includes a joint, for example, a ball joint or a universal joint, coupling the assembly to the support. The support includes two mounts for coupling to the joint and the distractor assembly is arranged for use with a patient in a supine position with the joint coupled to a first of the mounts for surgery on a right leg, or to a second of the mounts for surgery on the left leg.

According to another aspect, a method includes coupling a leg to a distractor assembly, positioning the leg in one of a distraction mode and a femoral acetabular impingement mode, and repositioning the leg in the other of the modes without the need for accessing a draped pelvis/thigh region.

According to another aspect, an apparatus includes a distractor member configured for coupling to patient table, and a leg mount coupled to the distractor for movement relative to the table by both sliding and threaded engagement.

According to another aspect, an apparatus includes a distractor member configured for coupling to patient table, a ball joint, and a leg mount coupled to the distractor member by the ball joint. The apparatus is configured such that relative movement between the foot mount and the table applies a distraction load to a patient. Embodiments of this aspect may include that the apparatus is configured to be entirely supported by a surgical table.

According to another aspect, an apparatus includes a distractor assembly configured to apply a distraction load to a patient including a ball joint or a universal joint for coupling the assembly to a surgical table.

Embodiments of this aspect may include that the joint is lockable, and that the apparatus is configured such that with a patient positioned on the surgical table and coupled to the distractor assembly, the joint is offset from the patient's hip joint.

According to another aspect, an apparatus includes a foot holder for use during surgery having a support bar configured and arranged to support a patient's lower leg.

According to another aspect, an apparatus includes a distractor member, a support configured to be fastened to a surgical table, and a joint coupling the distractor member to the support. The support includes at least two mounts for coupling to the joint.

According to another aspect, a method includes coupling a distractor member to a patient's leg, and dislocating the patient's hip by applying an adduction force to the patient's leg.

According to another aspect, a method includes coupling a distractor member to a patient's leg, and applying a distraction force with the distractor member to the patient's leg through a bent knee.

According to another aspect, an apparatus includes means for providing a distraction load on a leg in both supine and lateral positions of the leg.

According to another aspect, an apparatus includes means for repositioning a leg between a distraction mode and a femoral acetabular impingement mode without the need for accessing a draped pelvis/thigh region.

Advantages of the apparatus and method may include ease of positioning throughout the large range of motion required in FAI Mode, ease of repositioning between Distraction and FAI Modes, a single system that allows for both supine and lateral positioning, freeing the scrub nurse from holding the knee from falling laterally in FAI Mode, and less expensive than a fracture table.

The details of one or more embodiments of the invention are set forth in the accompanying drawings and the description below. Other features, objects, and advantages of the invention will be apparent from the description and drawings, and from the claims.

DETAILED DESCRIPTION

Figure 2:
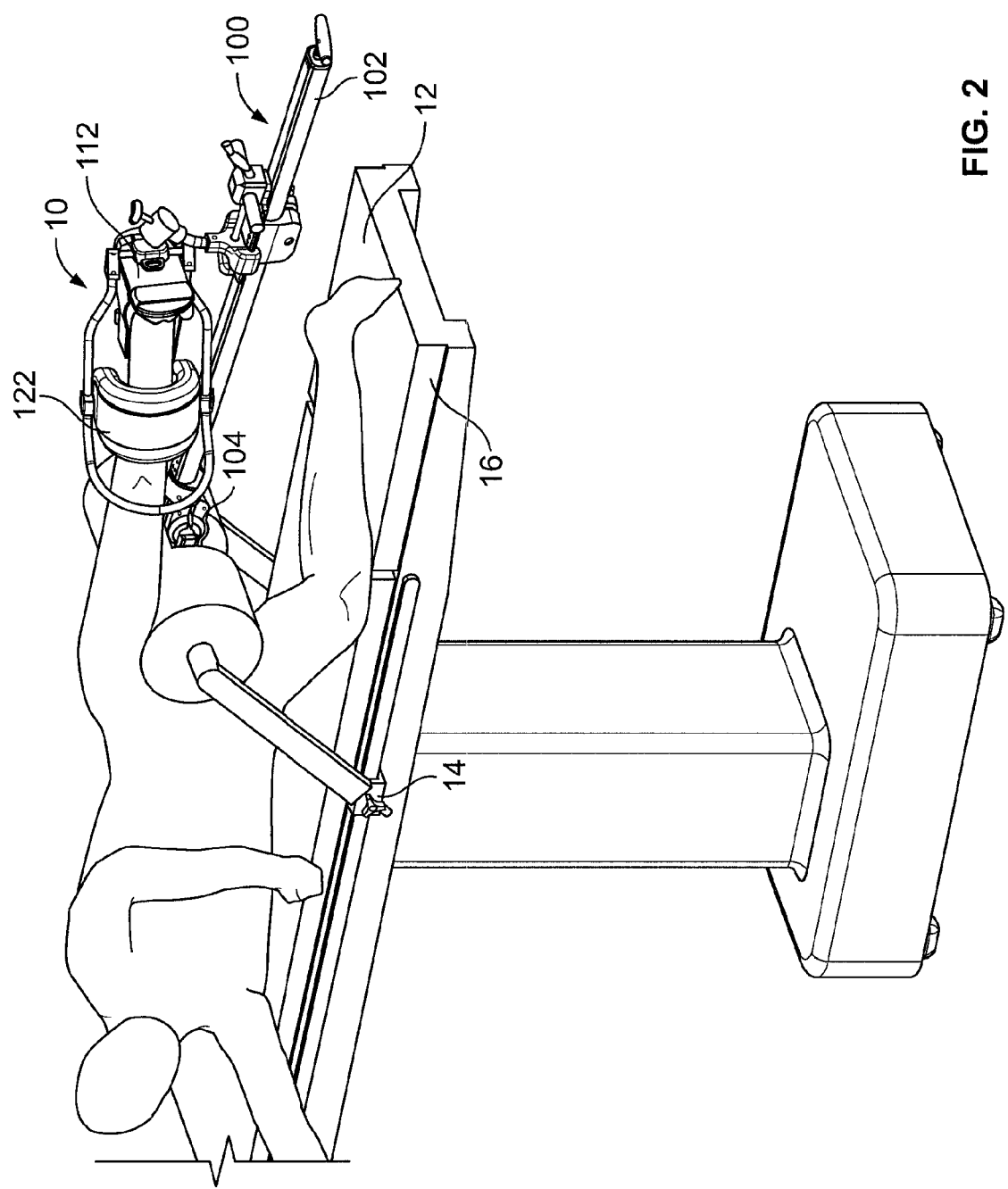
FIG. 2 illustrates the distraction assembly arranged for use in a Distraction Mode with the patient in a lateral position.
Figure 3:
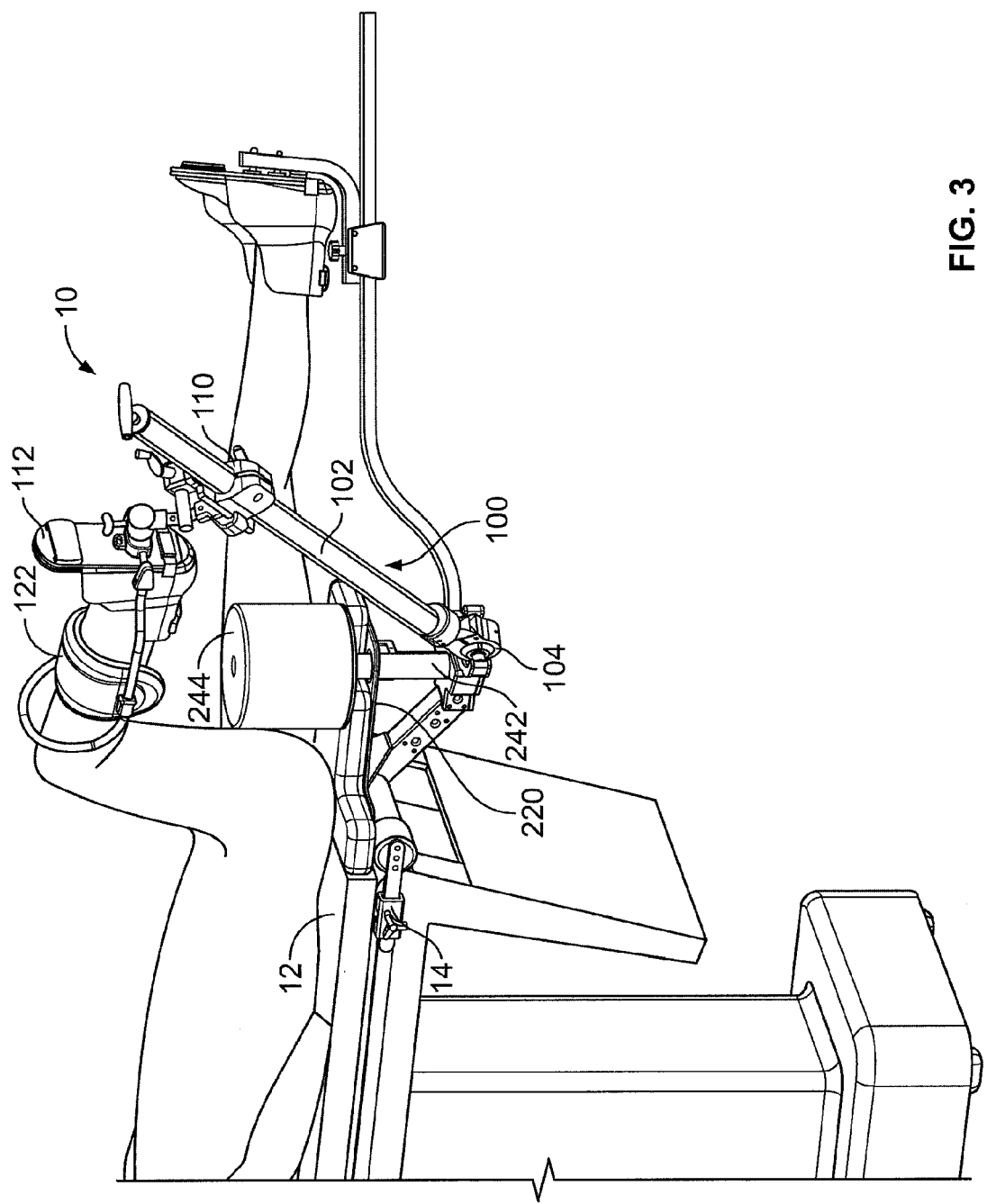
FIG. 3 illustrates the distraction assembly arranged for use in a FAI Mode with the patient in a supine position.
Figure 4:
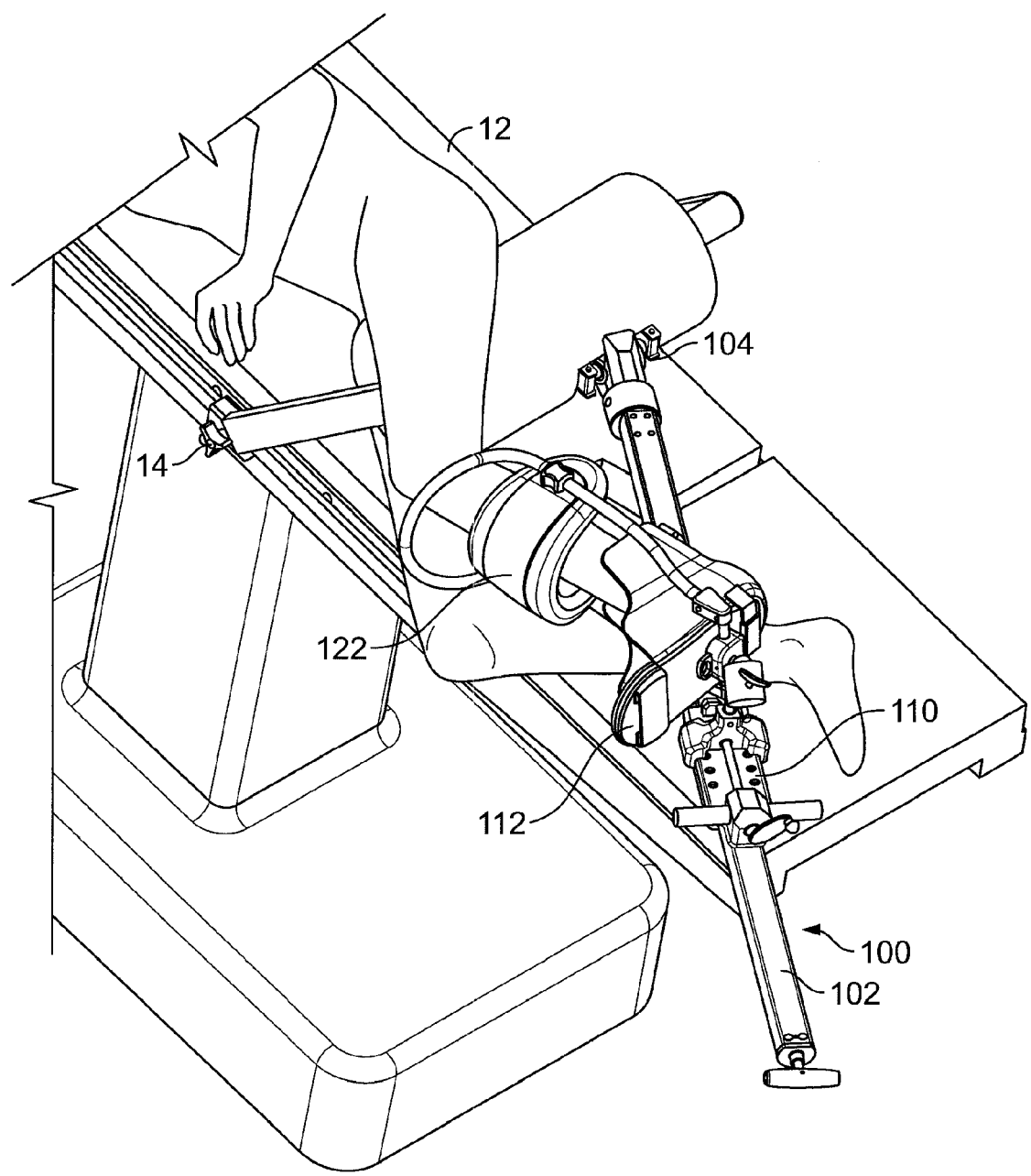
FIG. 4 illustrates the distraction assembly arranged for use in a FAI Mode with the patient in a lateral position.

Hip distraction is performed in either the Distraction Mode (FIGS. 1 and 2) or Femoral Acetabular Impingement (FAI) Mode (FIGS. 3 and 4) using a system 10 that can be attached to a standard operating table 12, such as found in hospitals and surgery centers, and that can accommodate both supine (FIGS. 1 and 3) and lateral (FIGS. 2 and 4) positioning of the patient. The system permits operating room personnel to reposition the patient between Distraction Mode and FAI Mode without needing to access the draped pelvis/thigh region.

Figure 5:
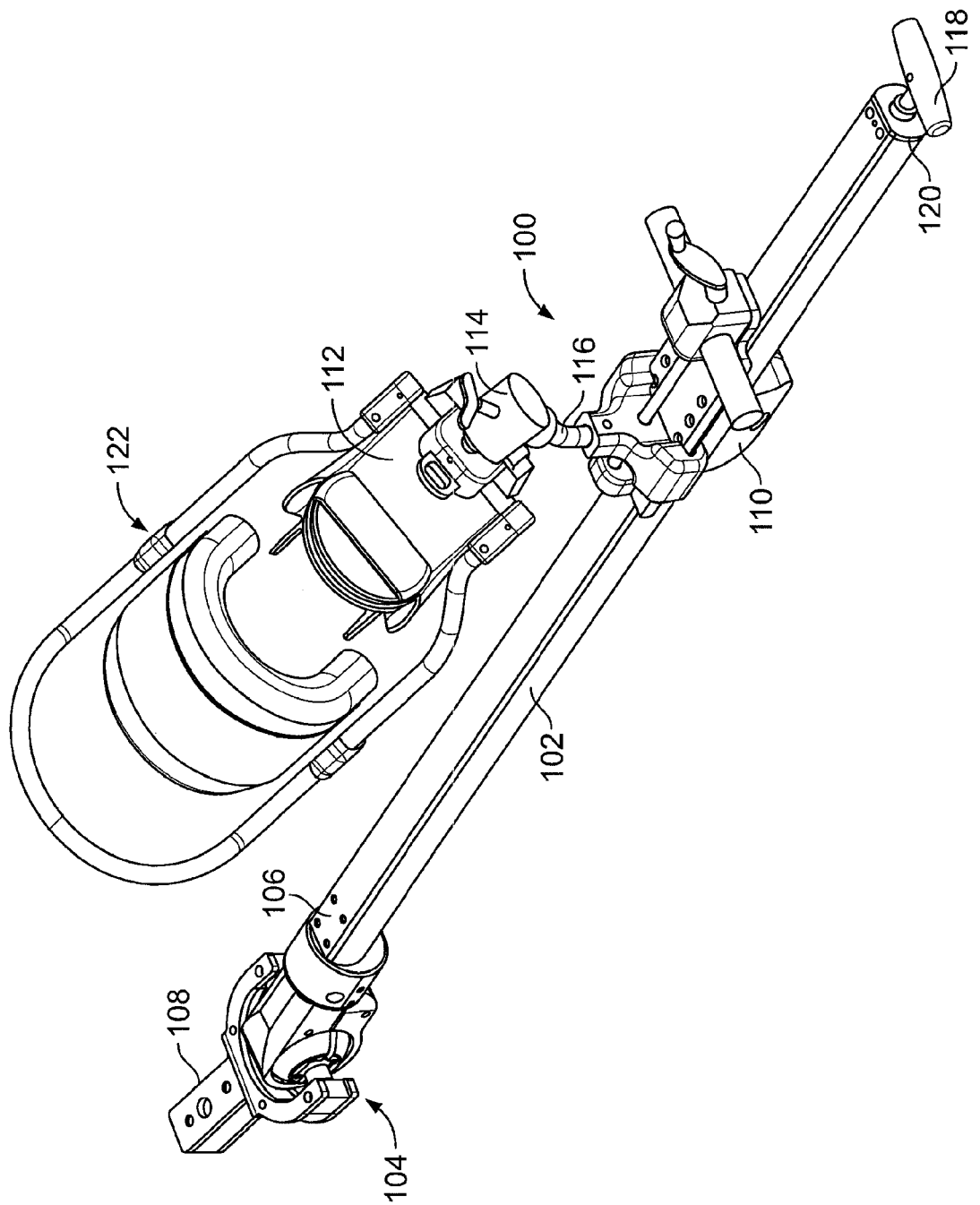
FIG. 5 is an isometric view of the distraction assembly and a foot holder attached to the distraction assembly.

Referring to FIG. 5, a distractor assembly 100 includes a distraction member, for example, a longitudinal spar 102 having a D-shaped cross-section, a lockable ball joint 104 (available from Allen Medical of Acton, MA and as seen in Allen Medical's Ultrafin stirrup products) attached to the proximal (pelvis) end 106 of the spar, a coupler 108 attached to the ball joint 104 for coupling the distractor assembly 100 to an operating room table, a slider 110 slidably mounted on the spar 102, and a leg mount, for example, foot mount 112, attached to slider 110 via a lockable ball joint 114 and a rigid, stationary arm 116. The ball joint 104 can be locked and unlocked by actuating a knob 118 located at the distal (foot) end 120 of the spar 102, thus allowing for the assembly to be unlocked and repositioned without need to access the draped pelvis/thigh region.

Figure 6:
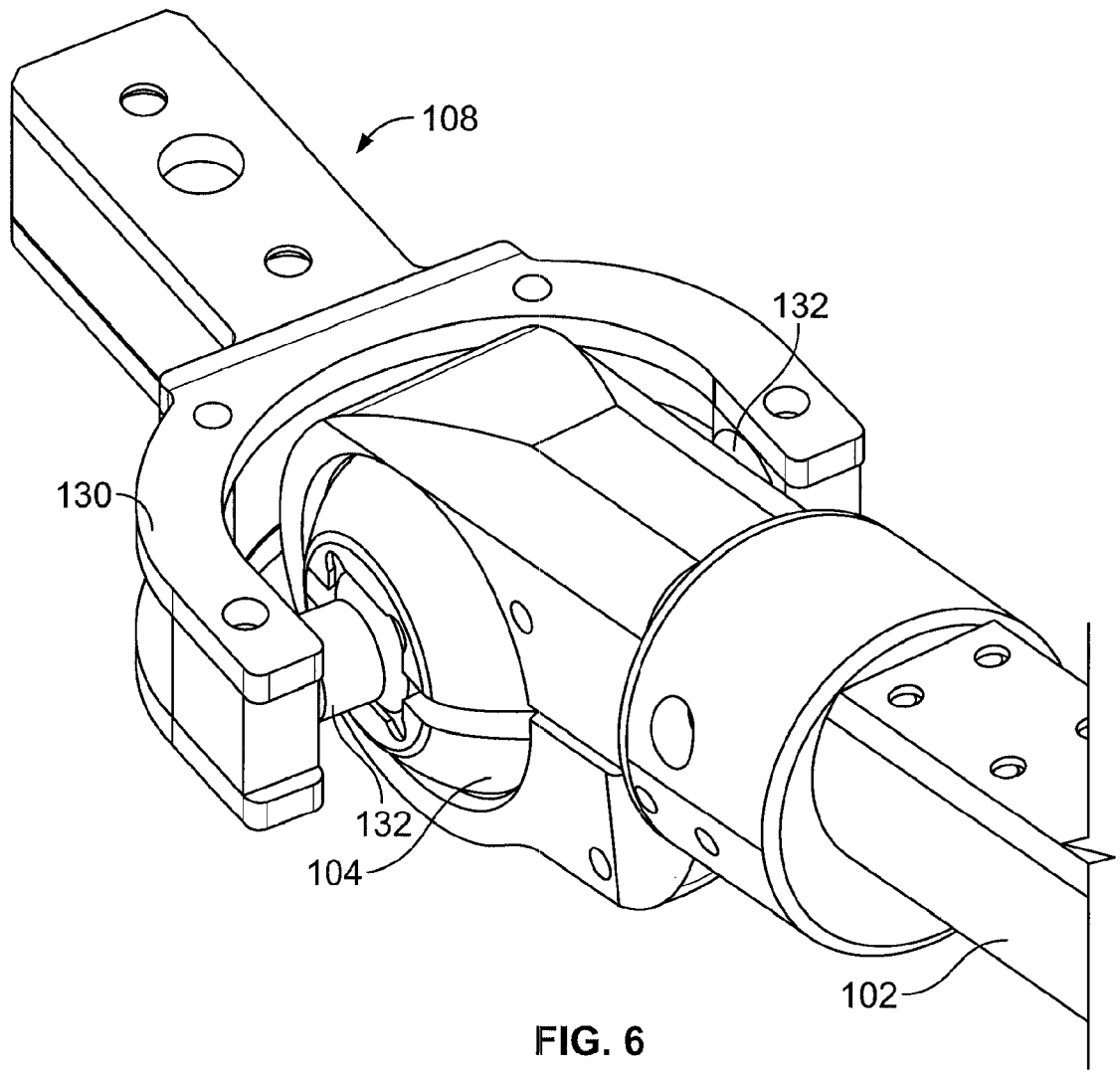
FIG. 6 is an isometric view of a ball joint of the distraction assembly.

The ball joint 104 and the coupler 108, as shown in FIG. 6, allows for a large range of hip motion, providing a full range of motion about the horizontal axis, and about 80 degrees of motion in the horizontal plane. The coupler 108 includes a yoke 130 that receives horizontally extending side arms 132 of the ball joint 104.

Figure 7:
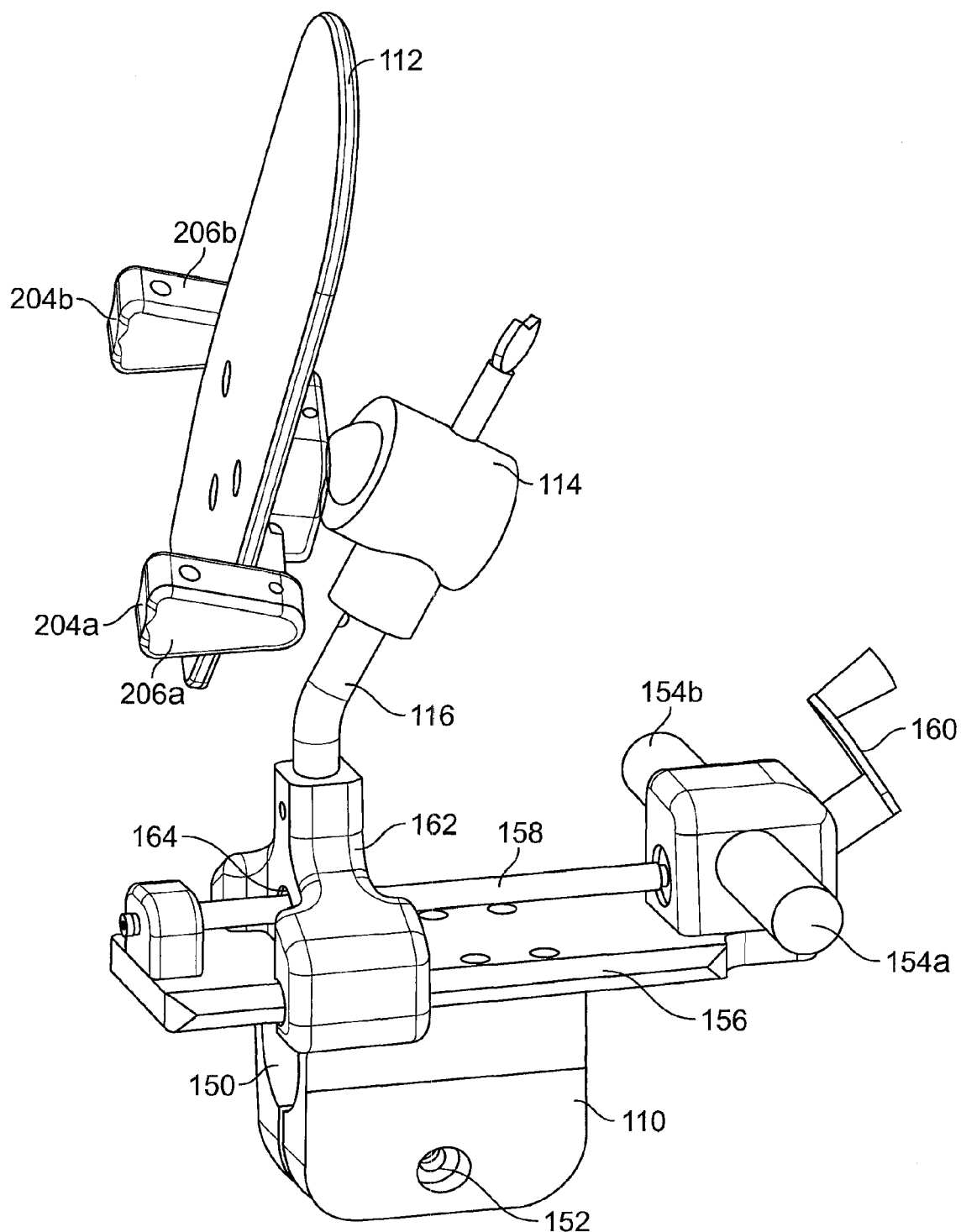
FIG. 7 is an isometric view of a slider and foot mount of the distraction assembly.

Referring to FIGS. 5 and 7, the slider 110 defines a D-shaped longitudinal through bore 150 that slidably and non-rotationally receives the spar 102, and a threaded, lateral through bore 152 that receives a locking bolt (not shown), that is tightened to lock the slider 110 to the spar 102. The slider 110 includes handles 154a, 154b that are used by the operating room personnel to slide the slider relative to the spar to provide gross distraction of the leg. For fine distraction, the slider 110 includes a base 156 supporting a threaded rod 158 attached to a turn handle 160. The base 156 also slidably supports a yoke 162 defining a threaded bore 164 through which the threaded rod 158 is received. By turning the handle 160, the yoke 162, and therefore the foot mount 112 attached to the yoke by the ball joint 114 and arm 116, can be moved back and forth relative to the base 156 to apply a desired amount of traction, for example, 25-150 pounds of force, to the leg.

Figure 8:
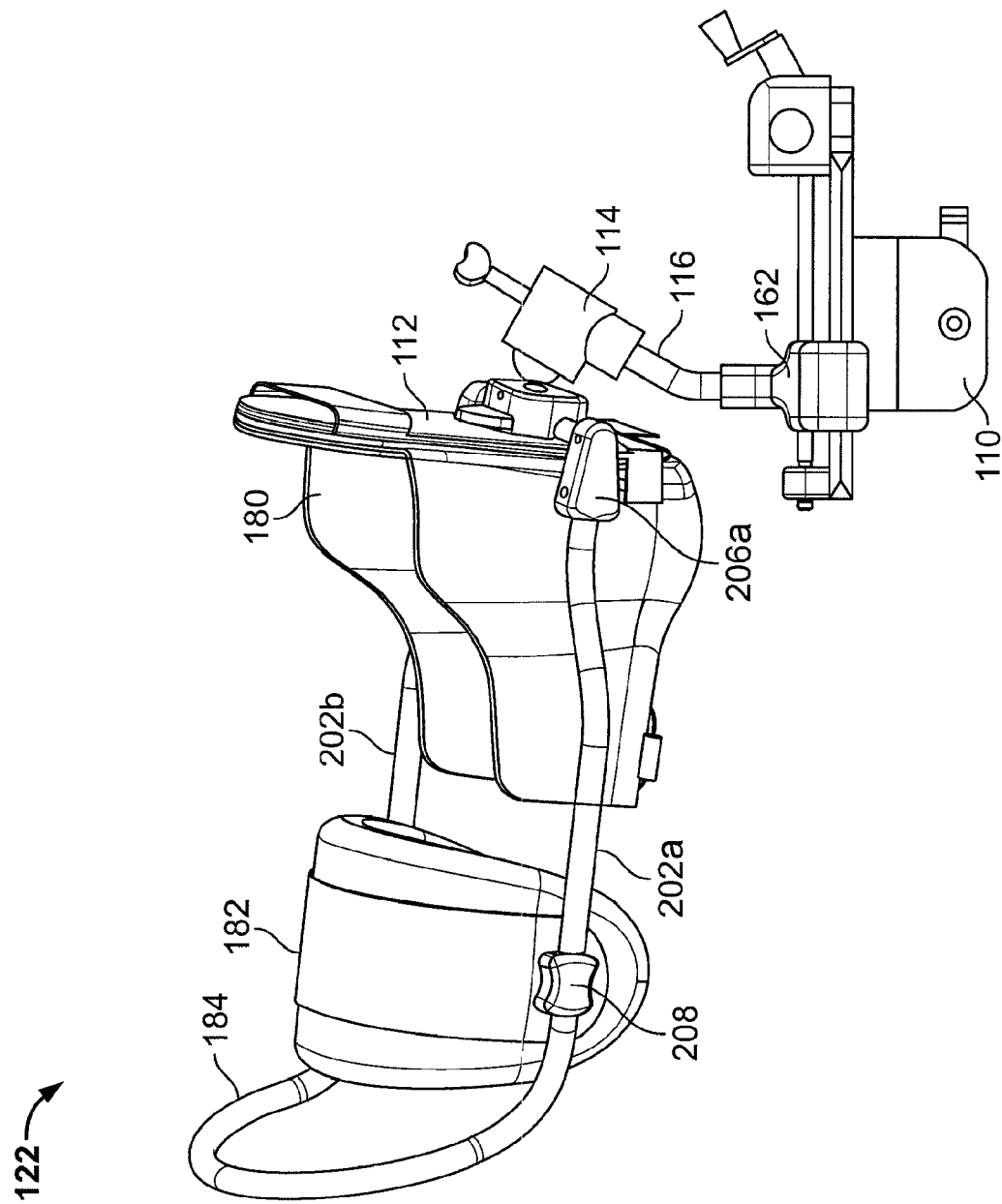
FIG. 8 shows the foot holder attached to the slider.
Figure 9:
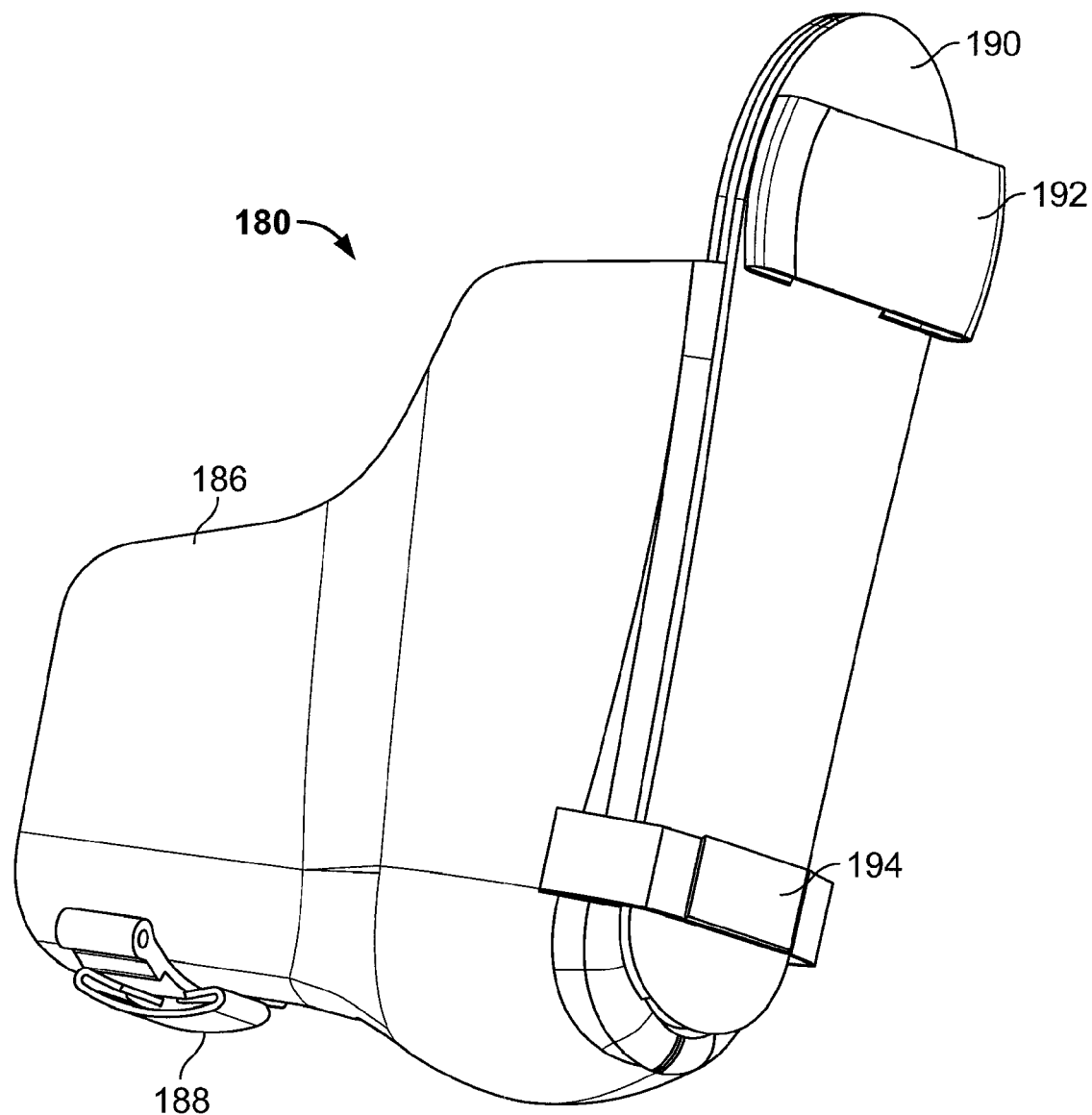
FIG. 9 is an illustration of a boot of the foot holder.

Attached to the foot mount 112 of the assembly 100 is a foot holder 122 (FIGS. 5 and 8). The foot holder 122 includes a boot 180, a shin support 182, and a support bar 184 that holds the upper tibia aligned with the foot. The support bar is particularly advantageous during FAI to stabilize the knee from falling laterally thus freeing the scrub nurse from having to hold the patient's leg in position. Referring also to FIG. 9, boot 180 includes a foot housing 186 with a tightening clasp 188, a sole 190, a U-coupling 192 that receives the foot mount 112, and straps 194 for securing the boot to the foot mount. The foot housing 186 has three straps, not shown, that go over the patient's forefoot and close the foot housing onto the foot.

The support bar 184 has two legs 202a, 202b, the ends of which are respectively received within openings 204a, 204b of foot mount couplers 206a, 206b (FIG. 7). The shin support 182 is attached to support bar 184 via shin mounts 208. The ball joint 114 and arm 116 permit the patient's leg to be finely positioned.

To support the patient's buttocks when the patient is in a supine position and to attach the distractor assembly 100 to the operating room table, a table extension 220 (FIGS. 1 and 10A) is employed. The table extension 220 includes a frame 222 with a cross bar 224, an angled strut 226, a Y-yoke 228, a vertical strut 230, and a platform 232. Extending from the cross bar 224 are two arms 234a, 234b that are used to attach the table extension to the operating room table 12 using rail clamps 14. The coupler 108 of the distractor assembly 100 plugs into one of a pair of female sockets 236a, 236b defined in Y-yoke 228 and is secured in place by a threaded locking knob (not shown). Since the ball joint 104 does not provide a large enough range of motion in the horizontal plane to accommodate surgery on both the right and left hips, socket 236a is used for surgery on the right hip, and socket 236b is used for surgery on the left hip, with the ball joint 104 providing the additional range of motion in the horizontal plane required for fine position of the leg.

Figure 1:
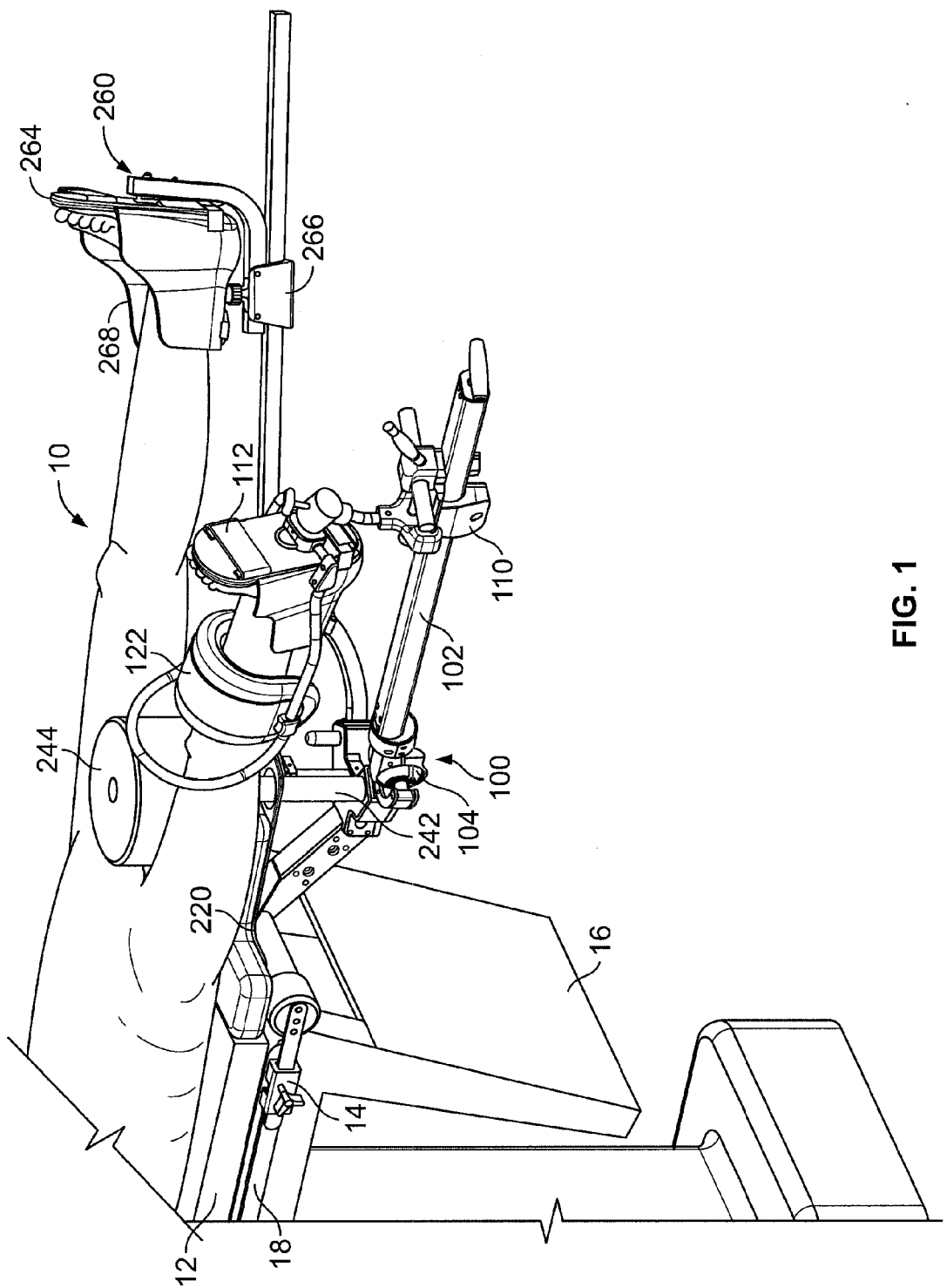
FIG. 1 illustrates a distraction assembly arranged for use in a Distraction Mode with the patient in a supine position.

The platform 232 is x-ray translucent and defines through holes 240a, 240b for receiving a post 242 (FIG. 1). The post 242 is received over a respective plug 244a, 244b of Y-yoke 228, and a peroneal pad 244 (FIG. 1) slips over the post 242. The post and pad provide the restraining force against the pelvis when the distraction force is applied to the leg. Through hole 240a is used for surgery on the right hip, and through hole 240b is used for surgery on the left hip. As shown in FIG. 10B, a pad 246 is attached to the platform 232. The pad defines a cut-out 248 permitting access to holes 240a, 240b.

Figure 10A:
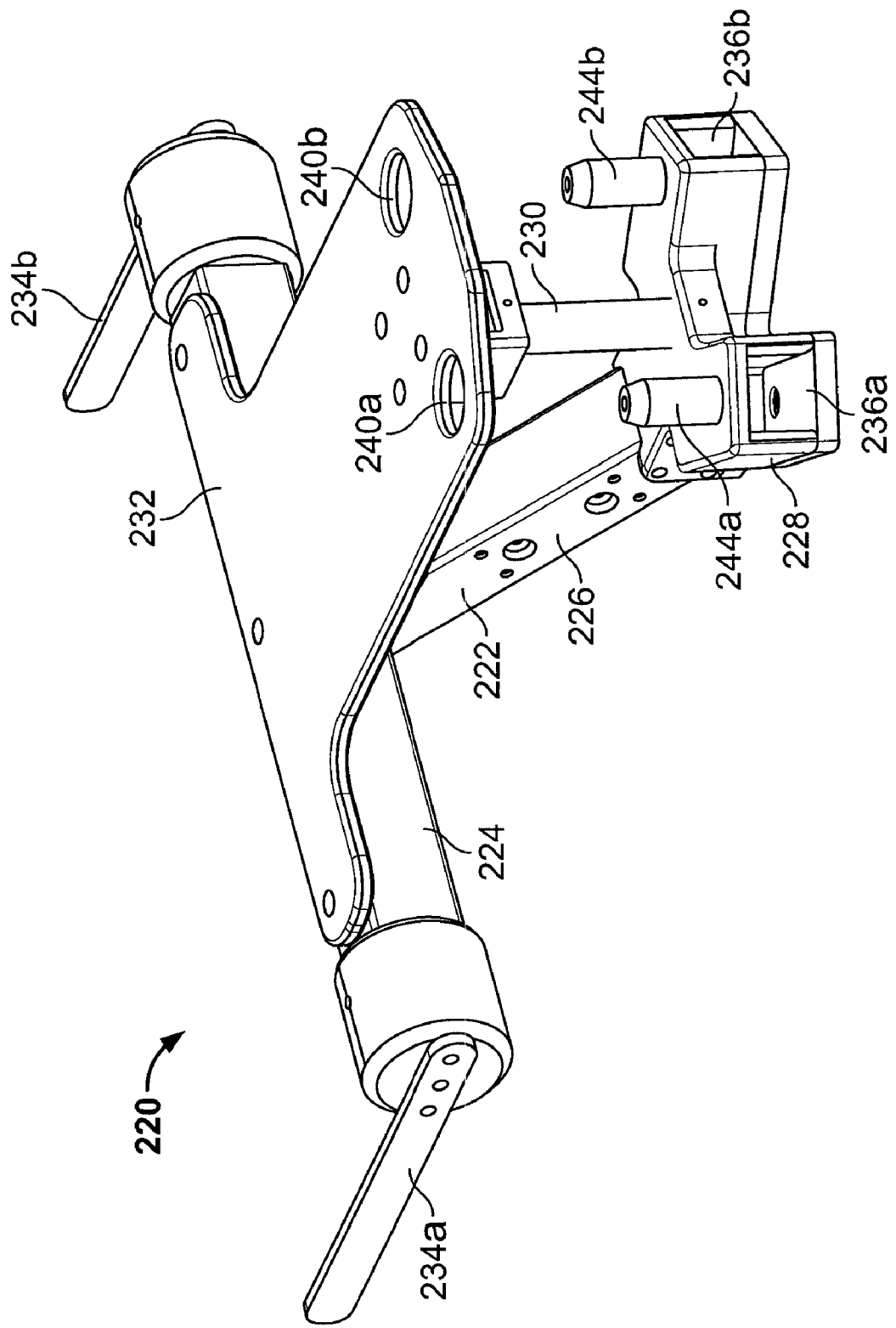
FIGS. 10A and 10B are isometric views of a table extension for mounting the distraction assembly to an operating room table with the patient in a supine position.
Figure 10B:
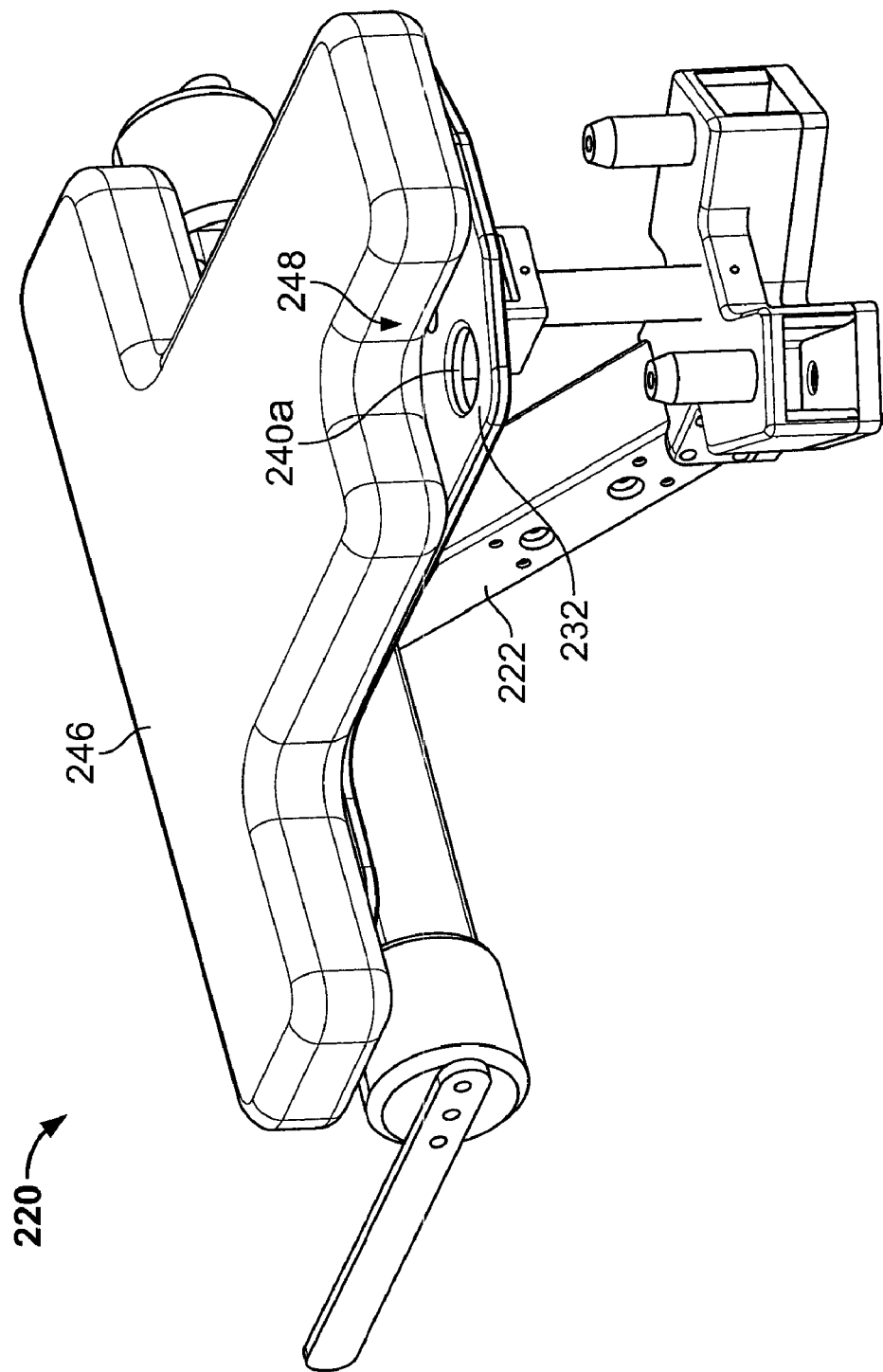
Figure 11:
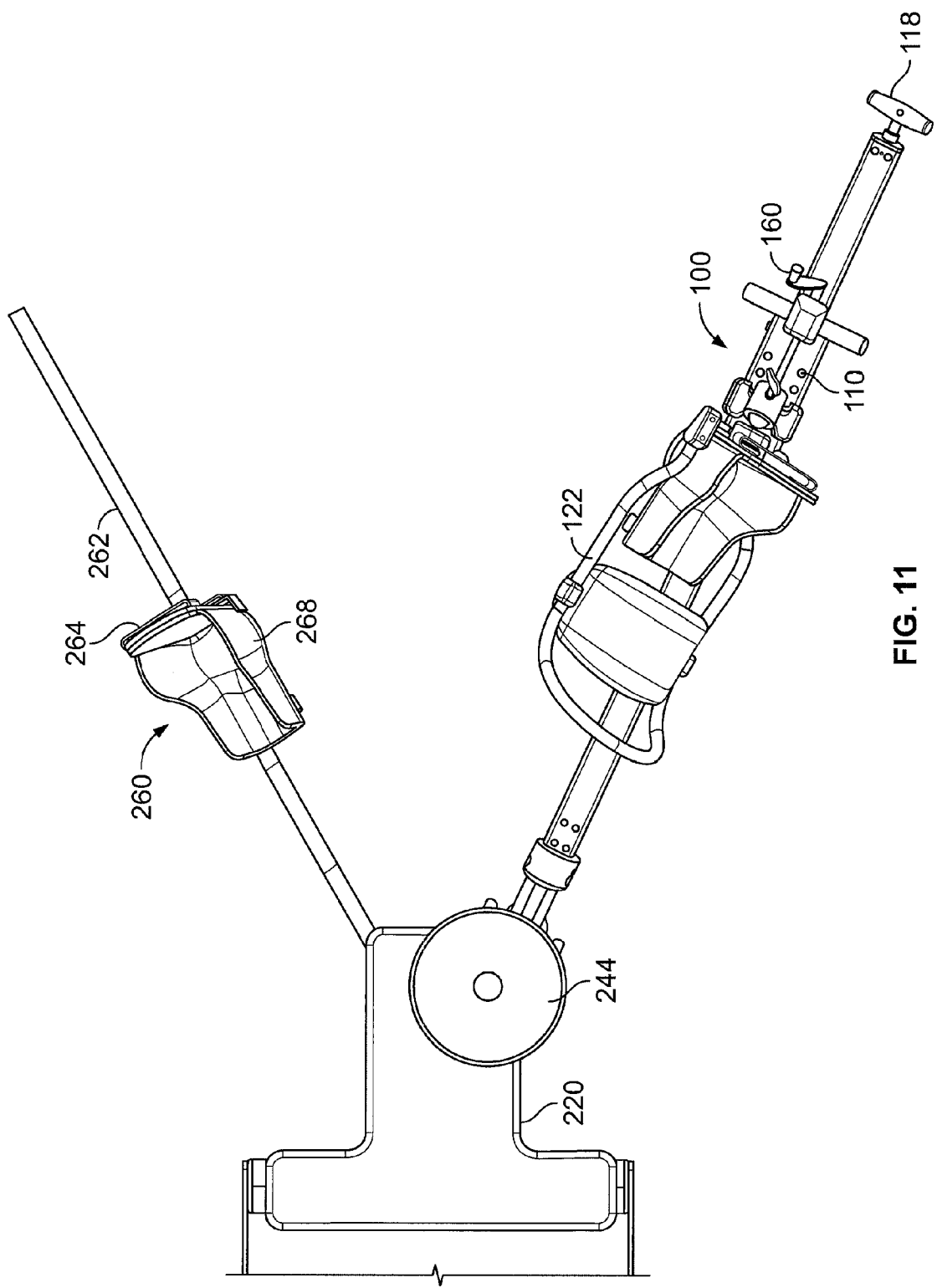
FIG. 11 is a top view of the distraction assembly also illustrating a non-operative leg holder for the supine position.

Referring to FIGS. 10A and 11, a non-operative leg holder assembly 260 is secured within the respective opposite socket 236a, 236b from that in which distractor assembly 100 is secured. Assembly 260 includes a spar 262 to which a foot mount 264 is slidably attached via a lockable slider 266 (FIG. 1). Attached to foot mount 264 is a boot 268 through which mild traction, for example, about 20 pounds can be applied to the non-operative leg.

To position the patient in the supine position for the Distraction Mode (FIG. 1), operating room personnel lower the operating room table's foot section 16 to the vertical position, clamp the table extension 220 to the side rails 18 of the table, and connect the distractor assembly 100 and leg holder 260 to the table extension. A patient transfer board (not shown) can be attached to the table extension to provide interim support to the legs while the feet are strapped into the boots 180, 268.

The operating room personnel then place the patient on the table, anaesthetize the patient, and attach the peroneal post and pad to the table extension. The patient is then brought down the table firmly against the peroneal pad, and the feet are wrapped in disposable foam booties (not shown) and strapped into the boots. The well leg is put under mild traction and the foot allowed to pivot into it's neutral position. The operating room personnel remove the patient transfer board and put the operative leg under initial traction by sliding the carriage 110 along the spar 102 until mild traction, for example, about 20 to 50 pounds, is achieved. The sliding carriage is then clamped to the spar. Further traction is achieved via the mechanical advantage of the threaded screw 158 between the carriage and boot. This distracts the hip via traction through the ankle and knee joints. The foot can be locked in any orientation (flexion or rotation) via the ball joint 114 between the boot and the threaded screw.

The surgeon then checks the distraction with fluoroscopy, places a drape over the patient, including covering the pelvis/thigh region of the patient, and places portals through the patient's skin leading to the hip joint under fluoroscopy control. As soon as the first portal is created the vacuum seal between the femoral head and acetabulum is broken and the joint distracts further. This can be aided by injecting fluid into the joint.

To move the patient from Distraction Mode to FAI Mode (FIG. 3), the operating room personnel reduce the traction force by turning the threaded screw 158 until no force is on the joint, unlock the ball joint 104, and lift the femur into flexion by raising the spar 102. Since the center of rotation of the spar, i.e., the ball joint 104, is located below the hip joint of the patient, the knee flexes as the spar is raised. The natural tendency of the knee to fall laterally is limited by the boot's lateral support bar 202a, 202b thus freeing the scrub nurse to help the surgeon.

Figure 12:
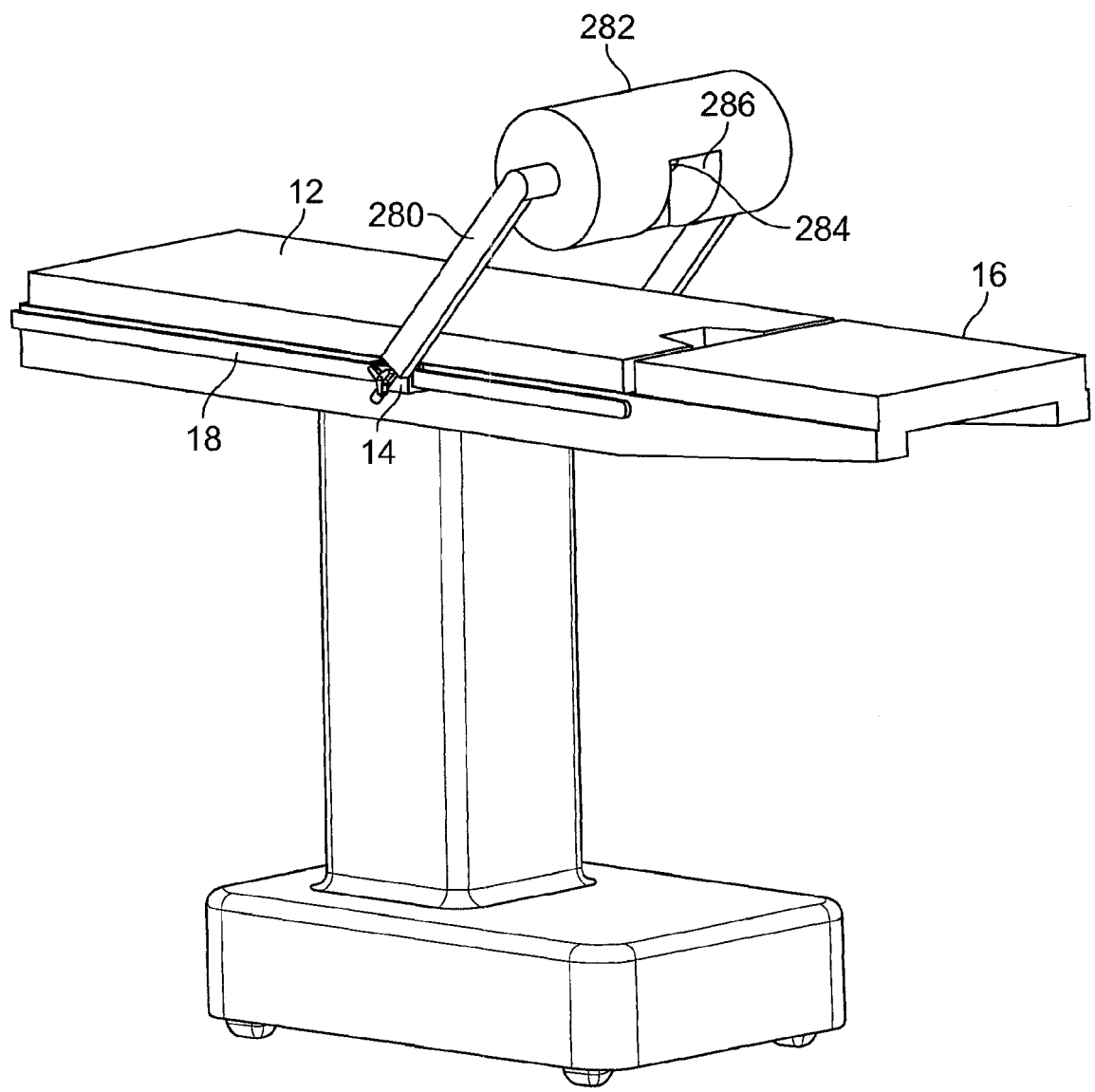
FIG. 12 is an isometric view of a lateral positioning table extension and pad.
Figure 13:
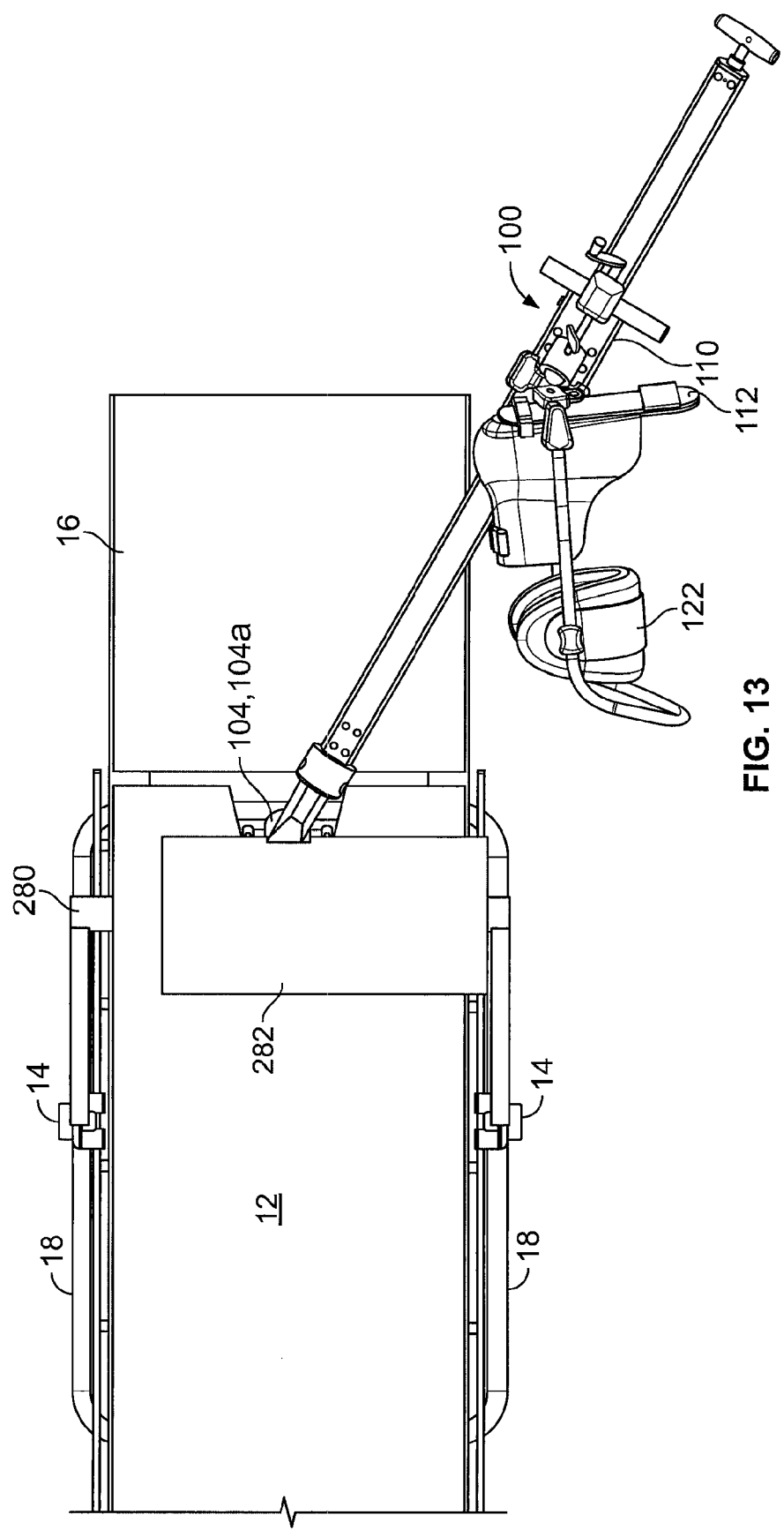
FIG. 13 is a top view of the distraction assembly arranged for lateral positioning.

Referring to FIGS. 12 and 13, for lateral positioning of the patient, the system 10 includes a "U" shaped peroneal bar 280 supporting a pad 282. The bar 280 has a socket 284 for receiving the coupler 108 (FIG. 5) of the distractor assembly 100, and the pad 282 defines a cut-out 286 for accessing socket 284. Bar 280 is attached to the side rails 18 of the operating room table 12 using clamps 14.

To position the patient in the lateral position for the Distraction Mode (FIG. 2), with the operating room table's foot section 16 up, the anaesthetized patient is rolled onto their side, the operating room personnel clamp the bar 280 to the side rails 18 with the pad 282 positioned between the patient's legs. To obtain lateral distraction, the operating room personnel raise the bar 280 by rotating the bar within the clamps 14 and lock the clamps. The distractor assembly 100 is then attached to the bar 280 and the operative leg wrapped in a disposable foam bootie (not shown) and strapped into the boot. As discussed above, gross distraction is achieved by moving the carriage 110 followed by fine distraction using the threaded screw 158. The boot can be positioned in any combination of flexion or rotation. There is no need for a non-operative leg holder as the non-operative leg is supported by the table's foot section 16.

To move between the Distraction Mode (FIG. 2) and FAI Mode (FIG. 4), the spar 102 is pivoted laterally about the ball joint 104. Since the center of rotation of the spar 102, i.e., the ball joint 104, is located distal to the hip joint of the patient, the knee flexes as the spar is moved laterally. The natural tendency of the knee to fall towards the floor is limited by the boot's lateral support bar 202a, 202b, thus freeing the scrub nurse to help the surgeon.

A number of embodiments of the invention have been described. Nevertheless, it will be understood that various modifications may be made without departing from the spirit and scope of the invention. For example, the distractor assembly can include a tensiometer to provide the surgeon with the distraction force. The slide and spar can be other than D-shaped, though preferably the slide and spar are configured such that the slide can slide along the spar without rotating. The ball joint 104 can be replaced with a two axis universal joint 104a (FIG. 13). Rather than locating screw thread 158 at slider 110, fine adjustment can be provided by a screw thread located, for example, between the ball 104 and the spar 102.

Figure 14:
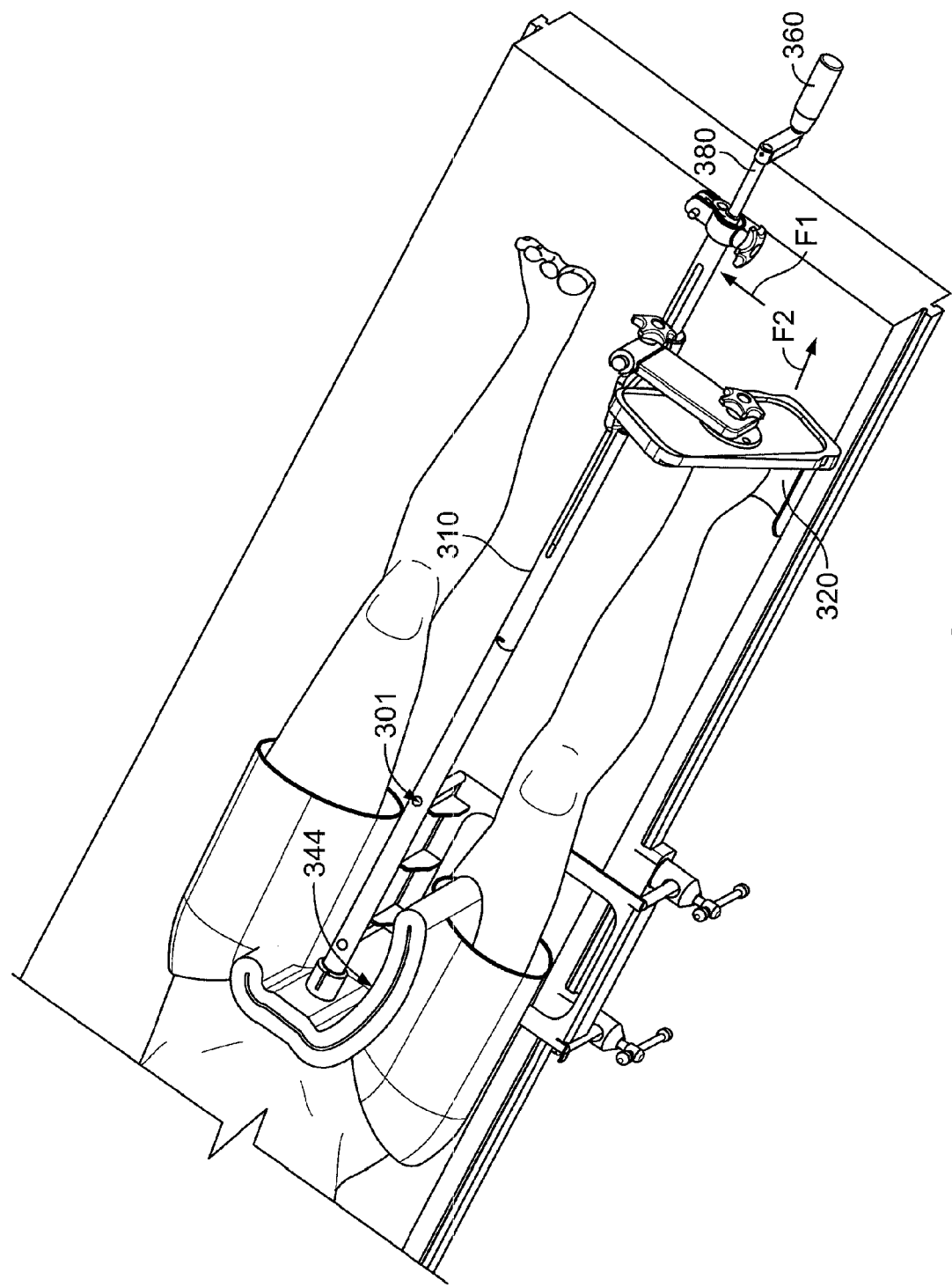
FIG. 14 illustrates an alternative embodiment of a hip distractor.

In an alternative configuration shown in FIG. 14, hip distraction is achieved via a pivoting action. Rather than using only axial force to dislocate the hip joint, a lever that pivots along the thigh translate a small foot adduction (movement towards the body centerline) into a large lateral hip distraction force. With a pivot 301 closer to the hip joint than to the foot end of a spar 310, a simple lever is created. The operative foot is held to the spar 310 by a boot assembly 320. Thus, when a small adduction force $F_1$ is applied to the spar 310 near the foot region, the mechanical advantage provided by the lever creates a larger lateral force at the hip joint. A peroneal pad 344 pushes laterally against the upper femur moving the femoral head of the hip joint. In addition to this lateral force, an axial force $F_2$ is imparted on the hip joint via traction through the boot assembly 320. This force can be achieved though turning of a crank 360 which is rotationally connected to a threaded rod 380. The boot assembly 320 is threaded to rod 380 but is limited from rotating by spar 310, thus boot assembly 320 moves axially when the crank 360 is turned. The peroneal pad 344 also provides a reaction force against the pelvis.

Figure 15:
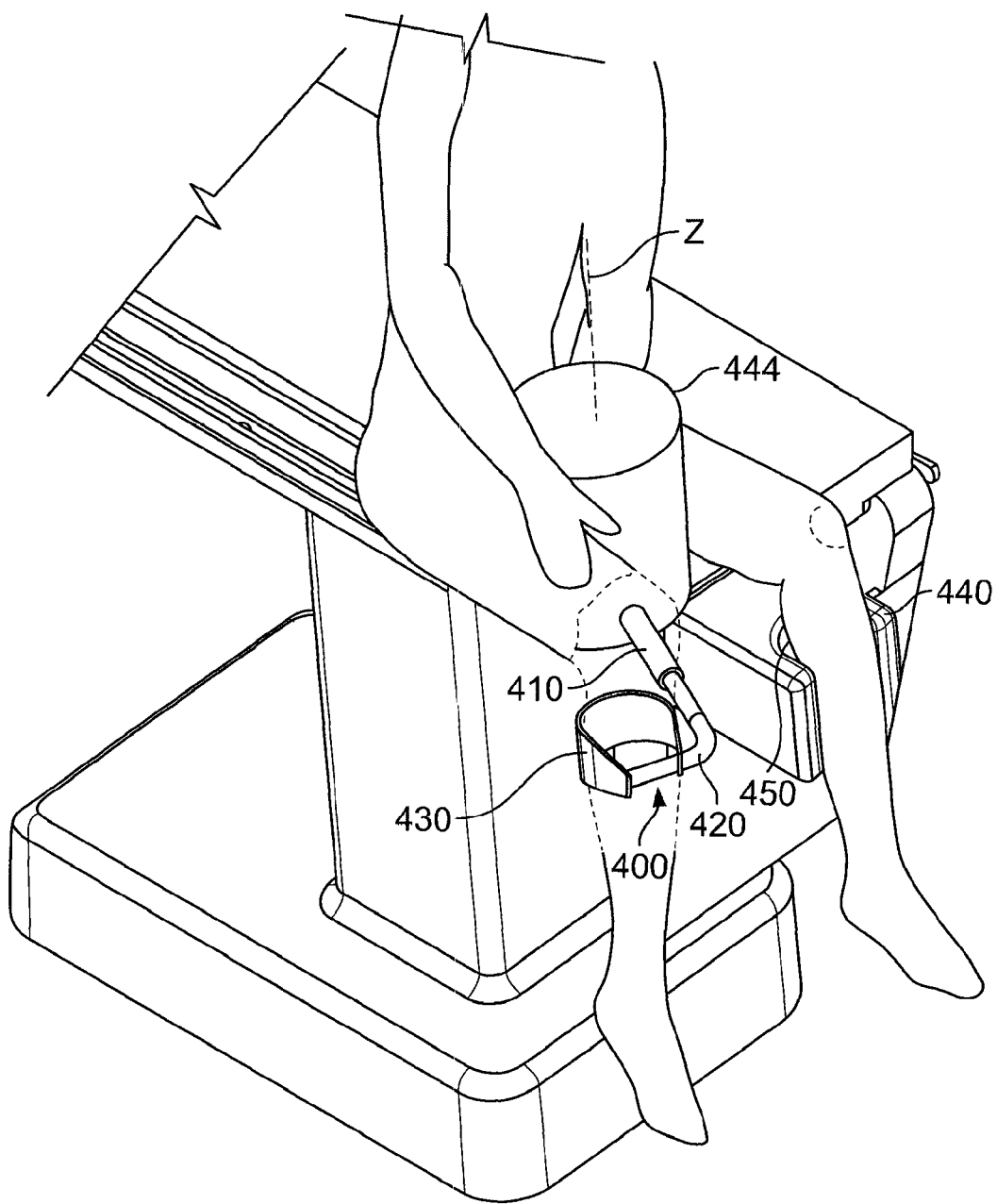
FIG. 15 illustrates another alternative embodiment of a hip distractor.

Referring to FIG. 15, distraction can be achieved through a bent knee providing a more compact distractor. With the operative leg bent approximately 90 degrees at the knee, the distraction force can be exerted at the knee. In addition, the reactive force that is borne through the non-operative leg can be reacted at the knee rather than through the ankle. Bent knee distraction of the operative leg is carried out by transmitting a distraction force to the upper tibia via a strap 430. The distraction force is transmitted through the knee to the femoral head. A peroneal pad 444 is connected to the surgical table and reacts the distraction force by pushing against the pelvis. A telescoping spar assembly 400 includes a bar 420, which is connected to a tube 410 by a slidable, lockable mechanism, such as a one-way ratchetting pawl.

When distraction is pulled on the operative leg, the pelvis tends to rotate around a vertical axis "Z" created by the peroneal pad. In order to minimize this pelvic rotation, a bent knee counter traction force is imparted upon the non-operative leg by a support 440. This force can be transmitted to the upper tibia via surface 450 which is then transmitted through the knee to the femoral head and pelvis. The support 440 can be fixed to the surgical table or it can telescope like spar assembly 400. If support 440 is fixed then the patient is moved proximally to create the counter traction force.

Accordingly, other embodiments are within the scope of the following claims.

What is claimed is:

1. An apparatus, comprising:
   a distractor assembly adapted to couple to a leg and capable of providing a distraction load on the leg in both supine and lateral positions of the leg, the distractor assembly including a single actuator configured to be manipulated to control movement of the distractor assembly about multiple axes;

side rail connectors coupled to the distractor assembly, the side rail connectors configured to attach to side rails of a surgical table; and a foot holder mountable to the distractor assembly and including a support bar configured to extend along a patient's upper tibia.

2. The apparatus of claim 1 wherein the distractor assembly comprises a joint and manipulation of the single actuator controls the joint.

3. The apparatus of claim 2 wherein the joint comprises a ball joint.

4. The apparatus of claim 2, wherein the actuator is located remote from the joint.

5. The apparatus of claim 2 wherein the joint comprises a universal joint.

6. The apparatus of claim 2 configured such that with a patient positioned on the surgical table and coupled to the distractor assembly, the joint is offset from the patient's hip joint.

7. The apparatus of claim 2 wherein manipulation of the single actuator locks the joint.

8. The apparatus of claim 2 wherein manipulation of the single actuator unlocks the joint.

9. The apparatus of claim 2 wherein manipulation of the single actuator locks and unlocks the joint.

10. The apparatus of claim 1 wherein the distractor assembly comprises a distractor member and a leg mount coupled to the distractor member for movement relative to the distractor member by both sliding and threaded engagement.

11. The apparatus of claim 10 further comprising a ball joint coupling the leg mount to the distractor member.

12. The apparatus of claim 11 further comprising, a ball joint located between the leg mount and the threaded engagement.

13. The apparatus of claim 10 wherein the leg mount comprises a foot mount.

14. The apparatus of claim 10 wherein,
the leg mount is movable over a majority of an entire length of the distractor member.

15. The apparatus of claim 1 further comprising:
a support coupling the distractor assembly to the side rail connectors, and
the distractor assembly includes a joint coupling the distractor assembly to the support, wherein the support includes two mounts for coupling to the joint.

16. The apparatus of claim 15 wherein the distractor assembly is arranged for use with a patient in a supine position with the joint coupled to a first of the mounts for surgery on a right leg, or to a second of the mounts for surgery on the left leg.

17. The apparatus of claim 15 wherein the joint comprises a ball joint.

18. The apparatus of claim 15 wherein the joint comprises a universal joint.

19. The apparatus of claim 15, wherein the support includes:
a crossbar connecting the side rail connectors to each other; and
a frame attached to the cross bar, wherein the two mounts for coupling to the joint are attached to the frame.

20. The apparatus of claim 1 wherein,
the distractor assembly includes a ball joint; and the apparatus further comprises a support for attaching to the surgical table, the support for coupling the surgical table to the distractor assembly through the ball joint, wherein the support includes the side rail connectors.

21. The apparatus of claim 20 wherein the ball joint is lockable.

22. The apparatus of claim 20 configured such that with a patient positioned on the surgical table and coupled to the distractor assembly, the ball joint is offset from the patient's hip joint.

23. The apparatus of claim 1 wherein the foot holder includes
a foot housing configured to be attached to a plate of a distractor assembly.

24. The apparatus of claim 23, wherein the foot housing includes toe and heel couplers.

25. The apparatus of claim 24, wherein the couplers comprise a u-coupling and a strap.

26. The apparatus of claim 1 wherein the distractor assembly comprises:
a distractor member,
a threaded engagement coupled to the distractor member,
a ball joint coupled to the threaded engagement, and
a leg mount coupled to the distractor member by the ball joint, the ball joint located between the leg mount and the threaded engagement, the apparatus configured such that relative movement between the leg mount and the table applies a distraction load to a patient.

27. The apparatus of claim 26, wherein with the side rail connectors coupled to the patient table, the apparatus is configured to be entirely supported by the patient table.

28. The apparatus of claim 1, wherein with the side rail connectors coupled to the surgical table, the apparatus is configured to be entirely supported by the surgical table.

29. The apparatus of claim 1 wherein the support bar is configured to support the upper tibia in the supine position.

30. The apparatus of claim 1 wherein,
the distractor assembly includes a universal joint; and the apparatus further comprises
a support for attaching to the surgical table, the support for coupling the surgical table to the distractor assembly through the universal joint, wherein the support includes the side rail connectors.

31. The apparatus of claim 1 wherein the actuator is located outside of a draped pelvis/thigh region.

32. The apparatus of claim 1
wherein the distractor assembly has a proximal end and a distal end;
a joint located at the proximal end of the distractor assembly;
and
a mechanism for locking the joint located at the distal end of the distractor assembly.

33. The apparatus of claim 1 further comprising:
a support configured to attach to side rails of a patient table, the support extending the patient table length to support a patient in a supine position, and the support including at least one mount for coupling a distractor assembly to the support.

34. The apparatus of claim 1 further comprising:
a first support including the side rail connectors and a coupler for mounting the distractor assembly thereto to provide a distraction load on the leg in a supine position of the leg; and
a second support including the side rail connectors and a coupler for mounting the distractor assembly thereto to provide a distraction load on the leg in a lateral position of the leg, the second support being different from the first support.

35. The apparatus of claim 1, further comprising a table extension attachable to the side rails and the distractor assembly, wherein the side rails are detachably coupled to the distractor assembly through the table extension.

36. An apparatus, comprising:
a leg support for use during surgery including a support bar configured to extend along a patient's upper tibia, the support bar having two terminal regions configured to mate to a distractor assembly and a shin support configured to laterally support a patient's lower leg.

37. An apparatus, comprising:
a bar configured to be fastened to side rails of a surgical table, the bar including a socket for coupling a distractor member to the bar; and
a pad connected to the bar and including a cut-out defined in the pad through which the socket is accessible for coupling the distractor member to the bar.

38. An apparatus, comprising:
a distractor assembly adapted to couple to a leg and capable of providing a distraction load on the leg in both supine and lateral positions of the leg, the distractor assembly including a single actuator configured to be manipulated to control movement of the distractor assembly about multiple axes;
side rail connectors coupled to the distractor assembly, the side rail connectors configured to attach to side rails of a surgical table; and
a table extension attachable to the side rails and the distractor assembly, wherein the side rails are detachably coupled to the distractor assembly through the table extension.

* * * * *

UNITED STATES PATENT AND TRADEMARK OFFICE
CERTIFICATE OF CORRECTION

PATENT NO. : 7,832,401 B2  
APPLICATION NO. : 11/289705  
DATED : November 16, 2010  
INVENTOR(S) : Paul Alexander Torrie, Edward J. Daley, II and Paul J. Skavicus It is certified that error appears in the above-identified patent and that said Letters Patent is hereby corrected as shown below:

On Title Page 2, Item 56, "OTHER PUBLICATIONS", insert --Quality, Reliability, and Innovation: Surgical Table Systems from STERIS Corporation, 2005 (4 pages).--.

On Title Page 2, Item 56, "OTHER PUBLICATIONS", insert --Steris-Amsco Orthovision Orthopedic Table, STERIS, 2002 (8 pages).--.

On Title Page 2, Item 56, "OTHER PUBLICATIONS", insert --International Search Report and Written Opinion for PCT/US2008/064611, dated September 2, 2008, 10 pages.--.

Signed and Sealed this  
Nineteenth Day of March, 2013

Teresa Stanek Rea  
*Acting Director of the United States Patent and Trademark Office*